United States Patent [19]
Requejo et al.

[11] Patent Number: 5,919,423
[45] Date of Patent: Jul. 6, 1999

[54] POLYMERIC WICK COMPOSITION FOR AIR FRESHENER CANDLE PRODUCT

[75] Inventors: Luz P. Requejo, Racine; Judith R. Zaunbrecher, Village of Wind Point, both of Wis.

[73] Assignee: S. C. Johnson & Son, Inc., Racine, Wis.

[21] Appl. No.: 08/915,160

[22] Filed: Aug. 20, 1997

[51] Int. Cl.[6] ............................... A61L 9/03; C10L 5/00
[52] U.S. Cl. .......................... 422/126; 422/305; 44/275; 431/288
[58] Field of Search ................................ 422/126, 5, 305; 44/275; 431/288

[56] References Cited

U.S. PATENT DOCUMENTS

| | | |
|---|---|---|
| 1,974,037 | 9/1934 | Atkins . |
| 2,090,297 | 8/1937 | Knoche . |
| 2,379,250 | 6/1945 | Muskat et al. . |
| 2,415,040 | 1/1947 | Rust et al. . |
| 2,818,615 | 1/1958 | Burness . |
| 2,829,511 | 4/1958 | Oesterle et al. . |
| 3,065,502 | 11/1962 | Lorenian . |
| 3,175,876 | 3/1965 | Fredericks ................................ 422/126 |
| 3,332,428 | 7/1967 | Mold et al. . |
| 3,351,695 | 11/1967 | Hollingsworth . |
| 3,499,452 | 3/1970 | Kallianos et al. . |
| 3,560,122 | 2/1971 | Cassar . |
| 3,577,588 | 5/1971 | Chisholm . |
| 3,630,697 | 12/1971 | Duling . |
| 3,705,890 | 12/1972 | Barker et al. . |
| 3,898,039 | 8/1975 | Lin . |
| 3,940,233 | 2/1976 | Fox et al. . |
| 4,092,988 | 6/1978 | Van Auken et al. . |
| 4,134,714 | 1/1979 | Driskill . |
| 4,155,979 | 5/1979 | Powell . |
| 4,278,658 | 7/1981 | Hooper et al. . |
| 4,302,409 | 11/1981 | Miller et al. . |
| 4,449,987 | 5/1984 | Lindauer . |
| 4,507,077 | 3/1985 | Sapper . |
| 4,568,270 | 2/1986 | Marcus et al. . |
| 4,663,315 | 5/1987 | Hasegawa et al. . |
| 4,708,851 | 11/1987 | Freytag Von Loringhoven . |
| 5,068,321 | 11/1991 | Buysch et al. . |
| 5,069,231 | 12/1991 | Rutherford . |
| 5,081,104 | 1/1992 | Orson, Sr. . |
| 5,313,002 | 5/1994 | De Heij et al. . |
| 5,320,798 | 6/1994 | Chambon et al. . |
| 5,538,018 | 7/1996 | Chan et al. . |
| 5,569,779 | 10/1996 | Sabahi et al. . |
| 5,645,845 | 7/1997 | Neumann et al. . |

FOREIGN PATENT DOCUMENTS 63-074440  4/1988  Japan .

*Primary Examiner*—Elizabeth McKane

[57] ABSTRACT

This invention provides a wick composition which is comprised of a polymeric strand such as polyethylene, which has a content of particulate polysaccharidic filler ingredient and air freshener ingredient. The wick is adapted for incorporation in a candle body. When the wick is ignited, it combusts with a controlled release of the air freshener ingredient into the atmosphere.

18 Claims, No Drawings

POLYMERIC WICK COMPOSITION FOR AIR FRESHENER CANDLE PRODUCT

BACKGROUND OF THE INVENTION

This invention generally relates to the dispensing of an air freshener from a candle product. More specifically this invention relates to a wick composition having a content of air freshener constituent which is released under wick combustion conditions.

Candles have been known and used since early civilization. A typical candle is formed of a solid or semi-solid body of wax such as paraffin wax or beeswax, and it contains an axially embedded combustible fibrous wick.

When the wick of a candle is lit, the generated heat melts the solid wax, and the resulting liquid flows up the wick by capillary action and is combusted.

More recently candles have been developed that appeal to the olfactory as well as the visual sense. This type of candle usually incorporates a fragrance oil in the wax body. As the wax is melted in a lighted candle, there is a release of the fragrance oil from the liquified wax pool.

Conventional fragrance candles have drawbacks because of cost and other considerations. The incorporation of fragrance oil in candlewax is difficult to achieve in a quantity which ensures the release of a suitable level of fragrance into the atmosphere during candle burning. Further, the incorporated fragrance tends to migrate and volatilize from the wax body prematurely. The fragrance also softens the wax body, and there is an undesirable loss of rigidity in the candle structure.

There is continuing interest in the development of improved fragrance and other types of air freshener candle products.

Accordingly, it is an object of this invention to provide an air freshener candle product which releases air freshener into the atmosphere only under the combustion conditions of the burning candle.

It is another object of this invention to provide a wick composition which has a content of air freshener constituent, and which is adapted for incorporation in a candle body.

It is a further object of this invention to provide a wick composition which can be produced by a continuous molding process.

Other objects and advantages of the present invention shall become apparent from the accompanying description and examples.

Publications of background interest relative to the present invention include U.S. Pat. Nos. 1,974,037; 2,090,297; 2,818,615; 2,829,511; 3,560,122; 3,630,697; and 3,940,233; incorporated by reference.

U.S. Pat. No. 2,829,511 describes a wick structure composed of a core strand of cellulose acetate in combination with an outer web of cotton fibers.

U.S. Pat. No. 3,560,122 describes a wick composition which is composed of paraffin wax, polyethylene, and particulate palygorskite clay.

DESCRIPTION OF THE INVENTION

One or more objects of the present invention are accomplished by the provision of a wick composition comprising a polymeric strand which contains (a) between about 2–40 weight percent of particulate polysaccharidic filler ingredient, and (b) between about 0.05–20 weight percent of air freshener ingredient.

The wick composition typically is an elongated strand having a diameter between about 0.2–0.8 centimeters.

In another embodiment this invention provides a candle product having an axial wick component which comprises a polymeric strand which contains (a) between about 2–40 weight percent of particulate polysaccharidic filler ingredient, and (b) between about 0.05–20 weight percent of air freshener ingredient.

The polymeric matrix of an invention wick composition preferably is selected from the class of thermoplastic resins which in general are adapted for fiber-formation by processes such as extrusion or compression molding. It is preferred that the polymer is composed of elements which do not convert into noxious vapors under wick combustion conditions, such as carbon, hydrogen and oxygen.

Equipment and processes for polymer fiber-formation by extrusion are described in publications such as U.S. Pat. Nos. 3,065,502; 3,351,695; 3,577,588; 4,134,714; 4,302,409; and 5,320,798; incorporated by reference. A wick polymeric strand can be composed of multiple filaments.

Suitable fiber-forming polymers include hydrocarbyl polyolefinic derivatives such as low and high density polyethylene, low and high density polypropylene, polybutene, polystyrene, and the like.

Other types of suitable polymers include polyvinyl acetate, and acrylate resins such as polymethyl acrylate, polymethyl methacrylate, polybutyl methacrylate, poly (ethyl acrylate/ethylene), and the like.

Other types of polymers such as thermoset resins can be utilized by pressure molding a powder blend of resin, polysaccharidic filler and freshener ingredients. Other components can be included in a wick composition such as stearic acid, polyoxyalkylene glycol, and the like.

The polysaccharidic filler ingredient of an invention wick composition typically is in the form of a powder, or in the form of fine fibers which have an average length between about 0.3–3 centimeters.

The term "polysaccharidic" as employed herein is meant to include natural products such as sugars, starches, hydrocolloid gums, cellulosics, and the like.

A cellulosic filler ingredient can be obtained from vegetable sources such as cotton, linen, flax, hemp, jute, wood pulp, and the like. A cellulosic filler can be in the form of substituted derivatives such as cellulose acetate or methylcellulose.

The term "cellulosic" as employed herein refers to a β-glucosidic polysaccharide corresponding to the formula:

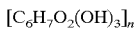

where n is an integer which provides an average molecular weight between about 100,000–2,000,000.

A present invention candle product can be produced by employing conventional candle making methods such as molding, dipping, and the like. The combustible body of a candle product typically is a thermoplastic blend of organic materials such as beeswax, paraffin wax, montan wax, carnauba wax, microcrystalline wax, fatty alcohols, fatty acids, fatty esters, natural and synthetic resins, and the like.

A wick normally extends longitudinally through a candle body. More than a single wick may be utilized in a spaced relationship, but usually a single wick component is centrally disposed in a shaped candle body. When a candle wick is ignited, the wick is adapted to combust gradually, so that both the wick and candle body are consumed.

When in a candle body, a present invention wick structure after ignition has sufficient porosity to absorb melted candlewax into the wick by capillary action for combustion during candle usage. The transport of melted wax can be enhanced by one or more capillary grooves extending axially along the surface of the wick filament.

The term "air freshener" as employed herein is meant to include fragrances such as geraniol, insect repellants such as citronellal, and therapeutic agents such as menthol.

An air freshener ingredient of a present invention wick composition can be any inherently volatile organic compound which is capable of being dispersed into the atmosphere when the wick composition is burning.

Suitable volatile air freshener compounds include limonene, α-terpinene, α-pinene, camphene, undecanol, 4-isopropylcyclohexanol, geraniol, linalool, citronellol, farnesol, menthol, 3-trans-isocamphylcyclohexanol, benzyl alcohol, 2-phenylethyl alcohol, 3-phenylpropanol, 3-methyl-5-phenylpentanol, cinnamic alcohol, isobomeol, thymol, eugenol, isoeugenol, anise alcohol, methyl salicylate, and the like.

Other suitable air freshener compounds include aldehydes and ketones such as hexanal, decanal, 2-methyldecanal, trans-2-hexenal, acetoin, diacetyl, geranial, citronellal, methoxydihydro-citronellal, menthone, carvone, camphor, fenchone, ionone, irone, damascone, cedryl methyl ketone, muscone, civetone, 2,4-dimethyl-3-cyclohexene carboxaldehyde, 2-heptylcyclopentanone, cis-jasmone, dihydrojasmone, cyclopentadecanone, benzaldehyde, phenylacetaldehyde, dihydrocinnamaldehyde, cinnamaldehyde, α-amylcinnamaldehyde, acetophenone, benzylacetone, benzophenone, piperonal, and the like.

Other suitable air freshener compounds include esters such as trans-2-hexenyl acetate, allyl 3-cyclohexylpropionate, methyl cinnamate, benzyl cinnamate, phenylethyl cinnamate, and the like.

Other suitable air freshener compounds include crystalline fragrance materials with a high vapor pressure, such as vanillin, ethyl vanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, proeugenol acetate, evernyl, and the like.

The present invention also contemplates a wick composition in which the air freshener is a constituent of a nonvolatile air freshener-release additive. The air freshener constituent is released by pyrolysis under wick combustion conditions.

The term "nonvolative" as employed herein refers to an organic compound which has a low vapor pressure under ambient conditions.

The chemical-bonding of a volatile alcohol air freshener such as geraniol or menthol to another organic compound to form a nonvolatile organic derivative can be accomplished by the formation of a carbonate ester linkage (as illustrated in Example V):

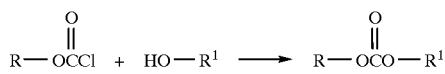

The chemical-bonding of an aldehyde such as citronellal or a ketone such as fenchone to another organic compound can be accomplished by the formation of a hemiacetal (ketal) and/or acetal (ketal) linkage under acidic conditions:

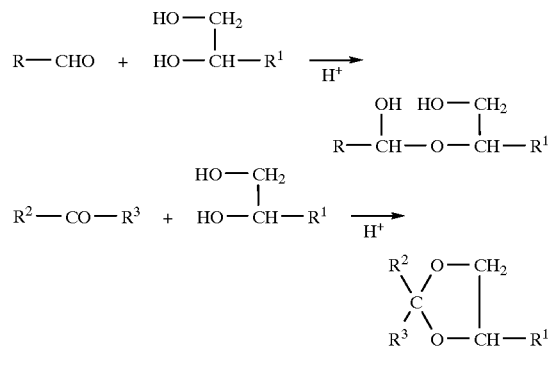

The chemical bonding of an ester such as phenylethyl cinnamate air freshener to another organic compound can be accomplished by a Michael addition reaction under alkaline conditions:

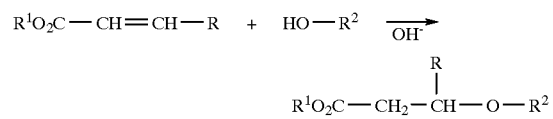

The Michael addition reaction is described in publications such as U.S. Pat. No. 2,415,040 and U.S. Pat. No. 5,569,779; incorporated by reference.

Another chemical means for forming a linkage between a volatile alcohol air freshener and another organic compound is by the use of an alcohol epichlorohydrin derivative under alkaline reaction conditions:

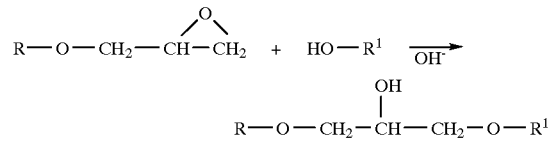

A present invention wick composition provides significant advantages not previously contemplated in the candle making art.

An invention wick composition can be manufactured efficiently in high volume by a continuous molding process such as by filament-forming extrusion.

The air freshener ingredient is released only when the wick composition is being combusted. The air freshener is released at a sustained constant rate.

Since there is no need for an air freshener such as a fragrance oil dispersed within a present invention candle product, there is no premature loss of air freshener by migration and evaporation from the candle body, and there is no softening or loss of rigidity in the candle body.

The following examples are fuirther illustrative of the present invention. The components and specific ingredients are presented as being typical, and various modifications can be derived in view of the foregoing disclosure within the scope of the invention.

EXAMPLE I

This Example illustrates the preparation of a wick composition in accordance with the present invention.

Cellulose powder is impregnated with geraniol, and the admixture is blended with polyethylene powder (MP 120°

C.). The blend contains 18 weight percent of cellulose powder and 1.5 weight percent of geraniol.

The blend is passed through an extruder under heat and pressure to form a continuous strand of wick composition having a 5 millimeter diameter, and having multiple capillary grooves axially along the strand surface.

A cut section of the strand is consumed completely when ignited. The wick combustion releases a flowery aroma which is characteristic of geraniol.

A shaped paraffin candle (MP 63° C.) is drilled down the center, and a wick section is inserted. When the wick is ignited, a flame persists until the candle is consumed. A flowery rose aroma is released during the candle burning.

Similar results are obtained when starch or guar gum is substituted for the cellulose powder.

EXAMPLE II

This Example illustrates the preparation of a wick composition in accordance with the present invention.

Polypropylene powder (MP 110° C.) is blended with an admixture of cellulose powder and ethylvanillin. The blend contains 22 weight percent of cellulose powder and 3 weight percent of ethylvanillin.

The blend is passed through an extruder under heat and pressure to form a continuous strand of wick composition having a 3 millimeter diameter, and having multiple capillary grooves axially along the strand surface.

A cut section of the strand is consumed completely when ignited. A sweet vanillin-like aroma is detectable in the atmosphere during the wick burning. A similar air freshener release is noted when the wick is burned within a candle body.

EXAMPLE III

This Example illustrates the preparation of nonvolatile air freshener-release saccharide derivatives of ketone and aldehyde air freshener constituents.

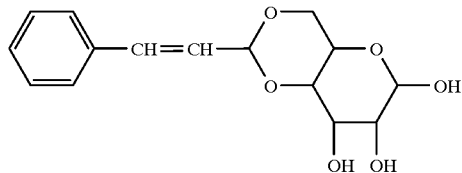

Glucose (180 g) is dissolved in dimethylformamide (4 liters), and Amberlite 1R-120 (100 g) is added. The mixture is heated to 80° C., and cinnamaldehyde dimethyl acetal (178 g) is added in portions over a three hour period. After the addition, the mixture is heated for an additional hour.

The ion exchange resin is removed by filtration, and the solvent and excess cinnamaldehyde dimethyl acetal are removed by vacuum distillation. The residual material is recrystallized from 95% ethanol to give 150 g of 4-6-0-cinnamylidene-D-glucopyranose product.

Following the same procedure, the D-glucopyranose acetal and ketal derivatives of the following aldehydes and ketones are synthesized:

| | |
|---|---|
| decanal | menthone |
| geranial | fenchone |
| citronellal | acetophenone |
| benzaldehyde | benzophenone |
| phenylacetaldehyde | camphor |
| dihydrocinnamaldehyde | geranylacetone |

Polyethylene powder (MP 120° C.) is blended with 10 weight percent of cellulose powder, and 2 weight percent of 4-6-0-cinnamylidene-D-glucopyranose air freshener-release additive. The blend is passed through an extruder under heat and pressure to form a continuous strand of wick composition having a 3.5 millimeter diameter.

A cut section of the strand is ignited, and the flame persists until the wick section is completely consumed. A faint scent of cinnamaldehyde is perceptible in the atmosphere. When a wick composition contains 4 percent of the air freshener-release additive, the aroma of cinnamaldehyde is strong and persistent. Similar olfactory results are obtained with each of the other synthesized aldehyde and ketone air freshener-release derivatives as additives in present invention wick compositions.

Similar air freshener release is obtained when a wick is burned within a candle body.

EXAMPLE IV

This Example illustrates the preparation of menthyl chloroformate.

A reactor in a dry-ice/acetone bath (−75° C.) is charged with liquid phosgene (117 g). Menthol (130 g), dissolved in 500 mL of cyclopentane, is added dropwise to the phosgene with stirring. The reaction medium is refluxed for six hours at room temperature.

The excess phosgene and cyclopentane are removed under reduced pressure. The recovered menthyl chloroformate is dissolved in diethyl ether (300 mL), and the solution is washed with aqueous sodium bicarbonate, and then with distilled water. The liquid medium is dried over sodium sulfate, and the solvent is removed under reduced pressure to yield a purified menthyl chloroformate.

EXAMPLE V

This Example illustrates the preparation of a nonvolatile air freshener-release dicarbonate ester of alcohol air freshener constituents.

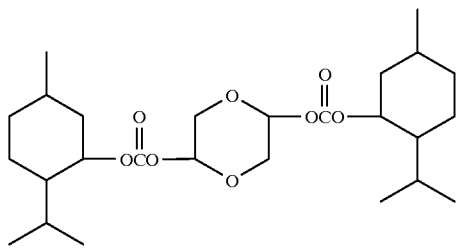

To a cooled solution of pyridine (25 mL) in chloroform (500 mL) is added with stirring glycolaldehyde (10 g, 0.167 mole). A solution of menthyl chloroformate (36.5 g; 0.167 mole) in chloroform (100 mL) is added dropwise. Stirring is continued for 30 minutes at 0° C., then for 18 hours at room temperature. The reaction medium is washed with aqueous sodium bicarbonate, and then dried over sodium sulfate.

The solvent is removed under reduced pressure. The residual product is recrystallized from chloroform:hexane to yield 16 g of 2,5-bis(menthylcarbonyloxy)-1,4-dioxane.

Following the same procedure, the dicarbonate ester derivatives of the following alcohols are synthesized:

| | |
|---|---|
| geraniol | eugenol |
| linalool | 3-phenylpropanol |
| citronellol | cinnamyl alcohol |
| benzyl alcohol | terpineol |

Polystyrene powder (MP 115° C.) is blended with 30 weight percent of cellulose powder, and 6 weight percent of 2,5-bis(menthylcarbonyloxy)-1,4-dioxane air freshener-release additive. The blend is passed through an extruder under heat and pressure to form a continuous strand of wick composition having a 4 millimeter diameter, and having multiple capillary grooves axially along the strand surface.

A cut section of the strand is ignited, and the flame persists until the wick section is completely consumed. A distinct aroma of menthol is detectable in the atmosphere. Similar olfactory results are obtained with each of the other synthesized aldehyde and ketone air freshener-release derivatives as additives in present invention wick compositions.

Similar air freshener release is obtained when a wick is burned within a candle body.

Similar results are obtained when the polymer ingredient is polyvinyl acetate.

What is claimed is:

1. A candle wick comprising a polymeric resin to which has been added
    (a) between 2–40 weight percent of particulate polysaccharidic filler ingredient, and
    (b) between about 0.05–20 weight percent of air freshener ingredient which is released only upon combustion of the wick.

2. A candle wick in accordance with claim 1 which is produced by a continuous molding process.

3. A candle wick in accordance with claim 1 wherein the polymeric resin is in the form of a filament which has at least one capillary groove extending axially along the filament surface.

4. A candle wick in accordance with claim 1 wherein the polymeric resin comprises a polyolefin.

5. A candle wick in accordance with claim 1 wherein the polymeric resin is selected from the group consisting of polyethylene and polypropylene.

6. A candle wick in accordance with claim 1 wherein the wick comprises multiple filaments.

7. A candle wick in accordance with claim 1 wherein the particulate polysaccharidic filler comprises powder or fine fibers.

8. A candle wick in accordance with claim 1 wherein the polysaccharidic filler is selected from the group consisting of sugars, starches, hydrocolloid gums and cellulosics.

9. A candle wick in accordance with claim 1 wherein the polysaccharidic filler comprises cellulose or a cellulose derivative.

10. A candle wick in accordance with claim 1 wherein the air freshener comprises a fragrance ingredient.

11. A candle wick in accordance with claim 1 wherein the air freshener comprises an insect repellant ingredient.

12. A candle wick in accordance with claim 1 wherein the air freshener comprises a therapeutic ingredient.

13. A candle wick in accordance with claim 1 wherein the air freshener ingredient comprises geraniol.

14. A candle wick in accordance with claim 1 wherein the air freshener ingredient comprises citranellol.

15. A candle wick in accordance with claim 1 wherein the air freshener ingredient comprises menthol.

16. A candle wick in accordance with claim 1 wherein the air freshener ingredient is in the form of a nonvolatile air freshener-release additive.

17. A candle wick in accordance with claim 1 which is an elongated polymeric strand having a diameter between about 0.2–0.8 centimeters, and which is adapted for incorporation in a candle product.

18. A candle product having an axial wick component which comprises a polymeric resin wick to which has been added (a) between about 2–40 weight percent of particulate polysaccharidic filler ingredient, and (b) between about 0.05–20 weight percent of air freshener ingredient which is released only upon combustion of the wick.

* * * * *

UNITED STATES PATENT AND TRADEMARK OFFICE
CERTIFICATE OF CORRECTION

Patent No.  : 5,919,423
Dated       : Jul. 6, 1999
Inventors   : Luz P. Requejo et al.

It is certified that errors appear in the above-identified patent and that said Letters Patent is hereby corrected as shown below:

Column 3, line 18, please substitute "isobomeol" with --isoborneol--.

Column 3, line 43, please substitute "evemyl" with --evernyl--.

Column 4, line 57, please substitute "fuirther" with --further--.

Signed and Sealed this

Seventeenth Day of April, 2001

Attest:

NICHOLAS P. GODICI

Attesting Officer

Acting Director of the United States Patent and Trademark Office